US012665071B2

(12) United States Patent
Raduchel

(10) Patent No.: US 12,665,071 B2
(45) Date of Patent: Jun. 23, 2026

(54) HIPAA PROTECTION FOR MEDICAL IMAGES

(71) Applicant: eIngot LLC, Great Falls, VA (US)

(72) Inventor: William J. Raduchel, Palo Alto, CA (US)

(73) Assignee: eIngot LLC, Great Falls, VA (US)

( * ) Notice: Subject to any disclaimer, the term of this patent is extended or adjusted under 35 U.S.C. 154(b) by 514 days.

(21) Appl. No.: 18/222,321

(22) Filed: Jul. 14, 2023

(65) Prior Publication Data

US 2025/0022578 A1    Jan. 16, 2025

(51) Int. Cl.
| | |
|---|---|
| *G06V 10/764* | (2022.01) |
| *G06T 7/00* | (2017.01) |
| *G06V 10/774* | (2022.01) |
| *G06V 10/776* | (2022.01) |
| *G06V 10/82* | (2022.01) |
| *G16H 30/20* | (2018.01) |
| *G16H 30/40* | (2018.01) |

(52) U.S. Cl.
CPC ........... *G16H 30/40* (2018.01); *G06T 7/0012* (2013.01); *G06V 10/764* (2022.01); *G06V 10/774* (2022.01); *G06V 10/776* (2022.01); *G06V 10/82* (2022.01); *G16H 30/20* (2018.01); *G06T 2207/20081* (2013.01); *G06T 2207/20084* (2013.01); *G06V 2201/03* (2022.01)

(58) Field of Classification Search
None
See application file for complete search history.

(56) References Cited

U.S. PATENT DOCUMENTS

| | | | | |
|---|---|---|---|---|
| 11,727,062 B1 * | 8/2023 | Gaskell | .................. | G06N 3/082 |
| | | | | 707/798 |
| 2023/0229803 A1 * | 7/2023 | Mozer | ..................... | G06T 7/194 |
| | | | | 726/26 |
| 2023/0334846 A1 * | 10/2023 | Wang | ..................... | G06V 10/82 |
| 2024/0265141 A1 * | 8/2024 | Rattner | .............. | G06F 21/6254 |
| 2025/0022578 A1 * | 1/2025 | Raduchel | .............. | G16H 50/70 |

* cited by examiner

*Primary Examiner* — Edward Park
(74) *Attorney, Agent, or Firm* — Fish & Richardson P.C.

(57) ABSTRACT

Methods, systems, and apparatus for receiving, from a provider server and at an image processing server, medical data including at least one image; determining, by the image processing server using a neural network, the at least one image within the medical data contains PII; in response to determining that the at least one image in the medical data contains PII, classifying, by the neural network, at least one medical characteristic of the image; generating, by the image processing server using the medical characteristic classification, at least one metadata tag that describes the medical characteristic; modifying, by the image processing server, the medical data to replace the image with the generated metadata tag; and transmitting, by the image processing server to a transaction server, the modified medical data.

20 Claims, 2 Drawing Sheets

HIPAA PROTECTION FOR MEDICAL IMAGES

BACKGROUND

The Health Insurance Portability Accountability Act (HIPAA) outlines requirements for physicians, caregivers, and insurance providers when handling healthcare Personally Identifiable Information (PII) in order to protect this information from fraud or theft. Violations of HIPAA can result in stiff financial penalties for the offending party.

SUMMARY

This specification relates to a system that provides HIPPA protections when handling medical imagery data. In some instances, medical data must be transferred to different parties within a healthcare system during the end-to-end process of administering care to a patient. For example, when submitting an insurance claim to a provider, the provider will generally require some form of evidence to verify the nature and scope of the care that was provided by the physician. Medical data is one form of evidence that can be used to verify the level of care.

However, precautions need to be taken to avoid violating HIPAA requirements when handling medical data that contains PII. For example, medical imagery data can fall under HIPAA protection if the images can be used to identify a specific patient. While imagery data can be helpful in efficiently and succinctly communicating a medical condition or status, sending of this imagery data to other parties (e.g., an insurance provider) presents financial risk to physicians if these parties are not equipped to handle PII in a manner that satisfies HIPAA requirements.

While physicians are capable of summarizing the nature of imagery data, as opposed to providing the imagery data directly, this process is time consuming and not practicable in view of the large amounts of patients that a physician may treat in the course of their practice. Moreover, written descriptions can be unreliable ways to communicate information clearly if they are not legible or if unfamiliar medical nomenclature is used. Delegating the responsibility of summarizing imagery data to an assistant or helper who is not a trained physician risks losing critical medical information in the resulting translation. Additionally, manually transcribing descriptions of medical data does not have the advantage of trend analysis and machine learning that can be performed by Artificial Intelligence techniques.

One technique that can be used to accurately, efficiently, and securely describe medical imagery data is the use of Artificial Intelligence (AI) to summarize this information such that it can be shared in manner that satisfies HIPAA requirements. For example, a neural network can be deployed to parse medical claims to determine if any images contain PII and replace any sensitive information with metadata tags that accurately and securely convey the medical characteristics present in the image. As a result, the provider is presented with information sufficient to expediently process a physician's claim, while the physician is protected from any penalties that would result from accidently sharing PII with an unauthorized party.

In some examples, this neural network operates in an image processing server that receives claims from caregiver servers prior to transmission to billing servers. Upon receiving the claim, the image processing server deploys the neural network to parse the claim for sensitive images, classify medical characteristics within the images, replace these medical characteristics with metadata tags, and forward the modified claim to the billing servers. In some examples, this process is made seamless for the caregiver such that when submitting a claim, the caregiver need only designate the intended end recipient of the claim (e.g., an insurance provider's billing server or service). In this example, the image processing server would intercept the claim traffic, perform any necessary processing, and release the claim to be transmitted to the originally indicated recipient.

The subject matter described in this specification can be implemented so as to realize one or more of the following advantages. The use of neural networks to process medial imagery data can prevent physicians from violating HIPAA requirements when sharing medical data with insurance providers and other parties, thus avoiding considerable financial penalties. Additionally, the use of these techniques will allow patients to have confidence that their healthcare provider or physician is adequately protecting their PII. The knowledge that such information is shared securely with these techniques will also streamline the claim process, as physicians will more confidently share corroborating information with providers. The use of AI to review medical imagery data can also identify medical and financial patterns and trends otherwise beyond the perception of a human being. Moreover, AI can identify patterns between medical conditions and characteristics by leveraging the combined learning experience gain by processing many claims and imagery data across a community of patients.

The details of one or more implementations of the subject matter described in this specification are set forth in the accompanying drawings and the description below. Other features, aspects, and advantages of the subject matter will become apparent from the description, the drawings, and the claims.

DETAILED DESCRIPTION

Figure 1:
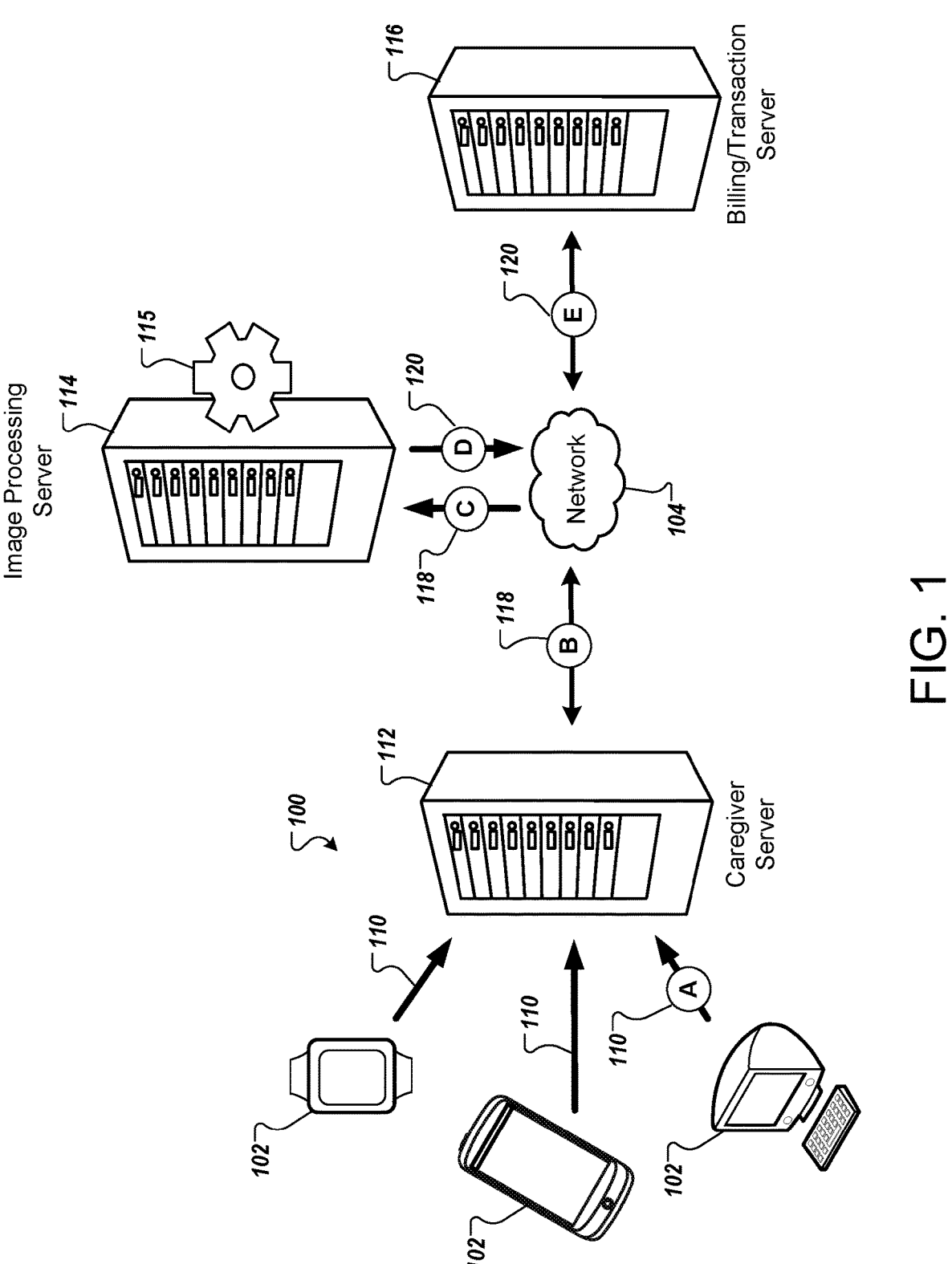
FIG. 1 is an example medical provider and transaction system.

FIG. 1 is an example medical provider and transaction system 100. The example system 100 includes various user devices 102, a network 104, a caregiver server 112, an image processing server 114, and a billing server 116.

In some examples, user devices 102 serve as the originating point for medical data. Examples of user devices include, but are not limited to, smartphones, desktop computers, wearable devices, smartwatches, monitoring devices, implanted devices, diagnostic equipment, scanning devices, or any other device suitable to collect medical data.

In some examples, a "caregiver" is an individual or entity involved in the healthcare of a patient. Some examples of caregivers include physicians, doctors, dentists, orthodontists, specialized practitioners, nurses, assisted living and nursing home personnel, and assistants for all of the previously mentioned roles. Other examples of caregivers are possible. When a caregiver collects medical data from a user device 102, this information is uploaded to a caregiver server 112 for electronic storage, processing, and further disposition. For example, a patient who has seen a doctor for a broken bone can receive an X-ray to allow the doctor to evaluate the extent of the injury. After collecting the X-ray from a machine 102, the resulting scans are then uploaded 110 ("A") to the doctor's server 112 for storage. In another example, a dermatologist may collect images of a patient's skin condition for record keeping. Because the dermatologist sees many patients, this particular patient's records are organized in a file specific to that patient on a server 112.

While the term "server" is used to describe the caregiver's data storage, it should be understood that the caregiver server 112 can also be any device that has suitable electronic storage and transmission capabilities. For example, a caregiver server 112 can also be the care giver's desktop computer, smart device, or a combination of these devices.

The caregiver server 112 is connected to a network 104 that allows communication to various other network destinations. For example, network 104 can be the internet, an intranet, a wireless network, or a cellular network.

The network 104 connects the caregiver server 112 to various billing servers 116. In some examples, billing servers 116 are associated with insurance providers that finance medical treatment for patients. While a "server" is used to describe billing server 116, like the caregiver server 112, various other electronic devices may perform the roles of the billing server 116 (e.g., a desktop computer, smart device, or a combination of these devices). In some examples, a billing server 116 can also be accessed by the caregiver server 112 through an electronic payment portal or application that is executing on the caregiver server 112, billing server 116, or another electronic device (not pictured).

In the previous example where X-rays are collected, a physician uploads an insurance claim 118 ("B") to the insurance provider's billing server 116 through network 104 to receive payment for the treatment. This claim includes evidence that corroborates the level of care the physician claims they provided to the patient. In this example, the physician includes the collected X-rays as this evidence. However, the X-ray in this example is PII as it identifies the particular patient from which it was collected. In many cases, the physician or caregiver server 112 may not have direct knowledge of all of the parties at the billing server 116 that handle or process the claim. If the billing server 116 or insurance provider personnel are not equipped to handle the PII in the transmitted claim 118, the sharing of the X-ray scans would result in a HIPPA violation and substantial financial penalties for the physician and insurance provider.

The image processing server 114 monitors the traffic from the caregiver server 112 to the billing server 116 over network 104 and detects the claim 118 ("C"). In some examples, the image processing server 114 monitors all network traffic from the caregiver server 112. In other examples, the image processing server 114 monitors only claims 118 that are submitted, or only traffic that has been flagged for review. When reviewing the claim 118, the image processing server 114 parses the claim 118 to determine if the claim 118 contains any images containing PII are present.

To parse the claim 118, the image processing server 114 deploys a neural network within an image processing algorithm (IPA) 115 capable of recognizing medical characteristics. The image processing server can employ any neural network suitable for feature recognition, for example, a convolutional neural network (CNN), a Recursive Cortical Network (RCN), or other types of neural networks suited for feature recognition.

When reviewing images, the IPA 115 examines the image to determine holistically if the image should be classified as containing PII. Once an image has been determined to contain PII, the IPA 115 then decides which features within the image are medically relevant by classifying medical characteristics within the image. For example, when reviewing an X-ray of a broken bone, the IPA 115 would identify the bone break as a relevant medical characteristic.

What medical characteristics are relevant can vary depending on the nature of the claim and associated imagery data. For example, medical characteristics classified by the IPA 115 can include bone breaks, lacerations or abrasions, medical conditions, or other features that a physician or provider would deem medically relevant. In addition to classifying the medical characteristic, the IPA 115 can also determine traits that describe the medical characteristic. For example, when reviewing a bone break, the IPA 115 can determine which bones are affected, as well as the type of fracture. Other examples of traits that can be identified include the severity, scope, or extent of a medical condition, the length or depth of a laceration, or other traits that would be relevant to determining the extent of a medical characteristic.

In some examples, to assist the IPA 115 in correctly identifying medical characteristics, the IPA 115 is trained on other instances of medical data and claims. For example, the IPA 115 can be provided with a training set of bone breaks along with the necessary information to correctly classify any relevant traits. In some examples, a generic set of training data is provided to the IPA 115 for initial training. In other examples, the IPA 115 can be continually trained and retrained on medical data it encounters during its use. For example, after generating a metadata tag defining a medical characteristic, the IPA 115 and image processing server 114 can receive correction data indicating that the classification and/or description of the medical characteristic generated by the IPA 115 is incorrect. In this case, the IPA 115 uses the correction data to retrain on the correct classification and/or description.

In some examples, the IPA 115 can reference previous relevant classifications of medical characteristics made in other instances of medical data for the same patient, a different patient, or a combination of patients. For example, when classifying a bone break in one patient, the IPA 115 can reference previous classifications of similar injuries in other patients to determine that this type of fracture will likely lead to further medical complications. Upon determining this correlation, the IPA 115 outputs a metadata tag that describes the relationship between the two classifications (e.g., the bone break in the one patient and the future complications from other patients). In this example, the IPA 115 creates a metadata tag that notes the high probability of future complications for this patient. The process of generating metadata tags is described in greater detail below. With this capability, physicians can leverage machine learning techniques to proactively identify trends in medical data that may otherwise be beyond human perception. Moreover, the financial data from trending claims can be used by insurance providers to improve their business analysis, for example, preemptively identifying that a patient may incur future medical costs for a specific injury or condition.

In some examples, the IPA 115 can reference narratives in the claim when determining which medical characteristics are relevant. For example, the IPA 115 can perform text recognition on the claim and determine the claim is being submitted for a broken bone. With this knowledge, the IPA 115 would then consider bone breaks within the image to be highly relevant and search for these features preferentially. In some examples, the IPA 115 assigns a weighting to relevant medical characteristics discovered through text recognition which are then used by the neural network in feature recognition.

After the IPA 115 has classified the medical characteristics and determined any relevant traits, the IPA 115 then generates metadata tags to describe the medical characteristics and traits. These metadata tags are then used to replace each instance of sensitive imagery data in the claim 118. This process is repeated for each medical characteristic within the imagery data of the claim 118. Once all metadata tags have been generated, the IPA 115 then modifies the claim 118 to generate a modified claim 120. The modified claim 120 is then transmitted to a recipient over network 104 by the image processing server 114 ("D"). In some examples, the image processing server 114 returns the modified claim 120 to the caregiver server 112 for review prior to transmission to the billing server 116 ("E"). In other examples, the image processing server 114 transmits the modified claim 120 to the billing server 116 in a seamless process.

Figure 2:
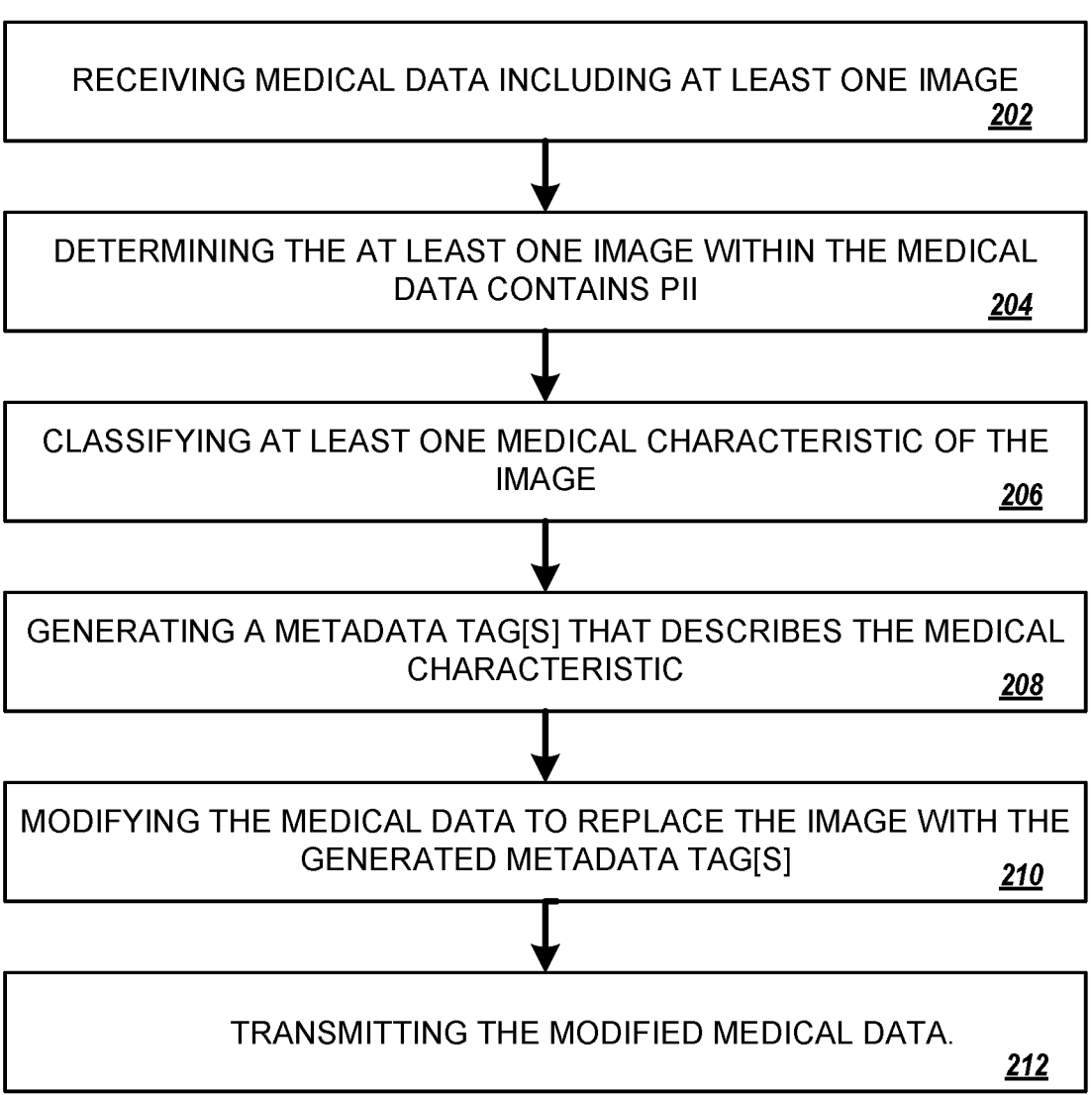
FIG. 2 is an example process for replacing medical images with metadata.

FIG. 2 is an example process 200 for replacing medical images with metadata. Process 200 includes receiving medical data, to include at least one image 202. As described with respect to FIG. 1, image data can originate from a variety of sources or devices.

Process 200 includes determining the at least one image within the medical data contains PII 204. As described with respect to FIG. 1, an image processing algorithm is deployed that can recognize sensitive images.

Process 200 includes classifying at least one medical characteristic of the image 204. As described with respect to FIG. 1, medical characteristics can be classified based on various factors, and what medical characteristics are relevant can depend on the nature of the claim. This step of process 200 is repeated for each medical characteristic within the image.

Process 200 includes generating at least one metadata tag that describes the medical characteristic 208. As described with respect to FIG. 1, the metadata tag describes the medical characteristic and any relevant traits. This step of process 200 is repeated for each medical characteristic within the image.

Process 200 includes modifying the medical data to replace the image with the generated metadata tag 210. As described with respect to FIG. 1, the metadata tag describes the medical characteristic and any relevant traits. This step of process 200 is repeated for each generated metadata tag.

Process 200 includes transmitting the modified medical data 212. As described with respect to FIG. 1, this transmission can be to a caregiver server for final approval, or to a billing server for disposition of the claim.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an operating environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g., a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

What is claimed is:

1. A computer implemented method comprising:

receiving, from a provider server and at an image processing server, medical data including at least one image;

determining, by the image processing server using a neural network, the at least one image within the medical data contains PII;

in response to determining that the at least one image in the medical data contains PII, classifying, by the neural network, at least one medical characteristic of the image;

generating, by the image processing server using the medical characteristic classification, at least one metadata tag that describes the medical characteristic;

modifying, by the image processing server, the medical data to replace the image with the generated metadata tag; and transmitting, by the image processing server to a transaction server, the modified medical data.

2. The method of claim 1, further comprising:

receiving, by the image processing server, correction data that indicates a classification, different from the classification determined by the neural network, to be used to generate the at least one metadata tag; and modifying, by the image processing server, the at least one metadata tag based on the correction data.

3. The method of claim 2, further comprising:

retraining the neural network on the received correction data.

4. The method of claim 1, wherein the neural network is trained on previous classifications made in other instances of medical data.

5. The method of claim 1, wherein the medical characteristic is a medical condition.

6. The method of claim 1, wherein the medical characteristic is the severity or scope of a medical condition.

7. The method of claim 1, further comprising:

determining, by the image processing server using a neural network, the classification of the medical characteristic is relevant to a previous classification made in another instance of medical data received by the image processing server; and generating, by the image processing server using a neural network, at least one metadata tag that describes a relationship between the two medical characteristic classifications.

8. The method of claim 1, wherein the neural network undergoes initial training on a set of example classifications.

9. The method of claim 1, further comprising:

receiving, by the image processing server, text associated with the image data;

determining, by the image processing server, that a medical characteristic is described by the text; and assigning, by the image processing server, a weighting to the medical characteristic described in the text to be used by the neural network when classifying medical characteristics present in the at least one image.

10. A system, comprising:

at least one processor; and a memory communicatively coupled to the at least one processor, the memory storing instructions which, when executed by the at least one processor, cause the at least one processor to perform operations comprising:

receiving, medical data including at least one image;

determining, using a neural network, the at least one image within the medical data contains PII;

in response to determining that the at least one image in the medical data contains PII, classifying, by the neural network, at least one medical characteristic of the image;

generating, using the medical characteristic classification, at least one metadata tag that describes the medical characteristic;

modifying, the medical data to replace the image with the generated metadata tag; and transmitting, the modified medical data.

11. The system of claim 1, further comprising:

receiving correction data that indicates a classification, different from the classification determined by the neural network, to be used to generate the at least one metadata tag; and modifying the at least one metadata tag based on the correction data.

12. The system of claim 11, further comprising:

retraining the neural network on the received correction data.

13. The system of claim 10, wherein the neural network is trained on previous classifications made in other instances of medical data.

14. The system of claim 10, further comprising:

determining the classification of the medical characteristic is relevant to a previous classification made in another instance of medical data received by the image processing server; and generating at least one metadata tag that describes a relationship between the two medical characteristic classifications.

15. The system of claim 10, wherein the medical characteristic is the severity or scope of a medical condition.

16. The system of claim 10, wherein the neural network undergoes initial training on a set of example classifications.

17. The system of claim 10, further comprising:

receiving text associated with the image data;

determining that a medical characteristic is described by the text; and assigning a weighting to the medical characteristic described in the text to be used by the neural network when classifying medical characteristics present in the at least one image.

18. One or more non-transitory computer-readable media storing instructions which, when executed by at least one processor, cause the at least one processor to perform operations comprising:

receiving, medical data including at least one image;

determining, using a neural network, the at least one image within the medical data contains PII;

in response to determining that the at least one image in the medical data contains PII, classifying, by the neural network, at least one medical characteristic of the image;

generating, using the medical characteristic classification, at least one metadata tag that describes the medical characteristic;

modifying, the medical data to replace the image with the generated metadata tag; and transmitting, the modified medical data.

19. The media of claim 18, further comprising:

receiving correction data that indicates a classification, different from the classification determined by the neural network, to be used to generate the at least one metadata tag; and modifying the at least one metadata tag based on the correction data.

20. The media of claim 19, further comprising:

retraining the neural network on the received correction data.

* * * * *